(12) United States Patent
Miao et al.

(10) Patent No.: US 10,563,268 B2
(45) Date of Patent: Feb. 18, 2020

(54) LONG NON-CODING RNA AND USE THEREOF IN DETECTION OF INTRAMUSCULAR FAT IN PIGS

(71) Applicants: Feng Shao, Qingdao (CN); Xiangyang Miao, Beijing (CN)

(72) Inventors: Xiangyang Miao, Beijing (CN); Wanlong Huang, Beijing (CN); Xiuxiu Zhang, Beijing (CN); Ai Li, Beijing (CN); Lingli Xie, Beijing (CN)

(73) Assignees: Feng Shao, Qingdao (CN); Xiangyang Miao, Beijing (CN)

( * ) Notice: Subject to any disclaimer, the term of this patent is extended or adjusted under 35 U.S.C. 154(b) by 0 days.

(21) Appl. No.: 16/223,145

(22) Filed: Dec. 18, 2018

(65) Prior Publication Data
US 2019/0194762 A1    Jun. 27, 2019

(30) Foreign Application Priority Data

Dec. 18, 2017 (CN) .......................... 2017 1 1365559

(51) Int. Cl.
*C07H 21/02* (2006.01)
*C07H 21/04* (2006.01)
*A61K 48/00* (2006.01)
*C12Q 1/6888* (2018.01)

(52) U.S. Cl.
CPC ..... *C12Q 1/6888* (2013.01); *C12Q 2600/124* (2013.01); *C12Q 2600/158* (2013.01); *C12Q 2600/178* (2013.01)

(58) Field of Classification Search
CPC .............................. A61K 38/00; C12N 15/111
See application file for complete search history.

(56) References Cited

U.S. PATENT DOCUMENTS 10,415,095 B2 * 9/2019 Wu ...................... A61K 31/713

* cited by examiner

*Primary Examiner* — Amy H Bowman
(74) *Attorney, Agent, or Firm* — Matthias Scholl P.C.; Matthias Scholl (57) ABSTRACT

A method of predicting variation of porcine intramuscular fat profile. The method includes detecting a BRCA1 gene and/or a JAML gene, or an expression product thereof. The disclosure also provides a method of selecting and breeding pigs. The method includes detecting a BRCA1 gene and/or a JAML gene, or an expression product thereof.

2 Claims, 3 Drawing Sheets

Specification includes a Sequence Listing.

LONG NON-CODING RNA AND USE THEREOF IN DETECTION OF INTRAMUSCULAR FAT IN PIGS

CROSS-REFERENCE TO RELAYED APPLICATIONS

Pursuant to 35 U.S.C. § 119 and the Paris Convention Treaty, this application claims foreign priority to Chinese Patent Application No. 201711365559.4 filed Dec. 18, 2017, the contents of which, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, Cambridge, Mass. 02142.

BACKGROUND

The disclosure relates to a long non-coding RNA (lncRNA) and use thereof in selective breeding of pigs.

LncRNA is a kind of RNA with a length of more than 200 nucleotides and no protein-coding ability. As regulatory non-coding RNA, lncRNA plays an important regulatory role in fat metabolism and adipogenic differentiation in pigs. Adipocyte differentiation includes three stages: inducing bone marrow stem cells (BMSCs) into preadipocytes, proliferation and growth of preadipocytes, and terminal differentiation into mature adipocytes. LncRNA can promote adipocyte differentiation.

SUMMARY

The disclosure provides a long non-coding RNA (lncRNA) XLOC_027632, having more than 90% sequence homology with SEQ ID NO: 1.

The lncRNA has more than 95% sequence homology with SEQ ID NO: 1. Particularly, the lncRNA has a sequence shown in SEQ ID NO: 1.

The term "homology", as used herein, primarily refers to the homology of sequence, which means that two or more proteins or DNA sequences have the same sources. Homologous sequences generally have similar functions. The homology between protein and DNA is often determined by the similarity of their sequences. The similarity refers to the proportion of identical sequences of DNA base or amino acid residues between the detection sequence and the target sequence in the sequence alignment. In general, when the similarity is higher than 50%, it is often assumed that the detection sequence and the target sequence may be homologous; when the similarity is less than 20%, the homology cannot be determined.

Further disclosed is a kit adapted to detect variation of porcine intramuscular fat profile, the kit being adapted to detect expression of the XLOC_027632 using a sequencing technique, a nucleic acid hybridization technique, or a nucleic acid amplification technique.

The expression of the XLOC_027632 is detected using a high-throughput sequencing technique, a probe hybridization technique, a gene chip technique or quantitative fluorescence PCR technique.

The nucleic acid amplification technique includes Polymerase Chain Reaction (PCR), Reverse Transcription Polymerase Chain Reaction (RT-PCR), Transcription-Mediated Amplification (TMA), Ligase Chain Reaction (LCR), Strand Displacement Amplification (SDA) and Nucleic Acid Sequence Based Amplification (NASBA). Among these techniques, the PCR requires reverse transcription of RNA into DNA (RT-PCR) prior to amplification, while the TMA and NASBA directly amplify RNA.

Typically, PCR uses multiple cycles of denaturation, annealing of primer pairs and opposite strands, and primer extension to exponentially increase the copy number of the target nucleic acid sequence; RT-PCR uses Reverse Transcriptase (RT) for preparation of complementary DNA (cDNA) from mRNA, and then the cDNA is amplified through PCR to produce multiple copies of the DNA; TMA autocatalytically synthesizes multiple copies of the target nucleic acid sequence under roughly constant temperature, ionic strength, and pH value; the multiple copies of the RNA of the target sequence autocatalytically synthesize additional copies, TMA arbitrarily blocks, and terminates, and modifies part of the sequences to improve the sensitivity and accuracy of the amplification process; LCR uses two sets of complementary DNA oligonucleotides that hybridize with the adjacent regions of the target nucleic acid. DNA oligonucleotides are covalently linked by DNA ligase in multiple cycles of heat denaturation, hybridization, and ligation to generate a detectable double-stranded oligonucleotide product; SDA is cyclically performed as follows: the annealing of the primer sequence pair from the opposite strand of the target sequence; the primer extension in the presence of dNTPaS to generate a double-strand hemiphosphorothioated product; the endonuclease mediated cleavage at a semi-modified restriction endonuclease recognition site, and the polymerase-mediated primer extension from the 3'-end of the cleavage site to produce a strand adapted to replace the existing strand for next cycle of annealing, cutting and displacement of the primer, thus geometrically amplifying the product.

The "Probe" as used in this disclosure refers to a molecule capable of binding to a sequence or subsequence or other portion of another molecule. Unless otherwise stated, the term "probe" generally refers to a polynucleotide probe capable of binding to another polynucleotide (often referred to as a "target polynucleotide") by complementary base pairing. Depending on the stringency of the hybridization conditions, the probe binds to a target polynucleotide that lacks complete sequence complementarity to the probe. The probe can be labeled directly or indirectly, and includes the primers. The hybridization methods include, but are not limited to, solution phase, solid phase, mixed phase or in-situ hybridization assay.

The probe has a base sequence complementary to a specific base sequence of a target gene, where the term "complementary" is not necessarily completely complementary as long as it can be hybridized. These polynucleotides usually have more than 80% of homology with respect to the specific base sequence, particularly, more than 90%, more particularly, more than 95%, and further particularly, 100% homology. These probes may be DNA or RNA, and may also be polynucleotides obtained by substituting part or all sequences of the DNA or RNA by artificial nucleic acids such as PNA (Polyamide Nucleic Acid), LNA (Locked Nucleic Acid, Bridged Nucleic Acid), ENA (2'-O,4'-C-Ethylene-bridged nucleic acids), GNA (Glycerol nucleic acid), TNA (threose nucleic acid).

The term "hybridization" in this disclosure refers to the pairing of complementary nucleic acids. The strength of hybridization and hybridization (i.e., the strength of association between nucleic acids) is affected by the following factors such as the degree of complementarity between nucleic acids, the stringency of the reaction conditions, the G:C ratio and the melting temperature of the formed hybrid.

The single molecule containing complementary nucleic acid pairs within its structure is referred to as "self-hybridizing."

Also provided is a kit adapted to detect variation in porcine intramuscular fat profile, the kit being adapted to detect expressions of the lncRNA, the kit comprising a pair of primers for nucleic acid amplification, and sequences of the pair of primers are represented by SEQ ID NO: 2 and SEQ ID NO: 3.

The kit is adapted to detect a tissue comprising intramuscular adipose tissue.

The disclosure also provides the following applications of the lncRNA:

A method of using the long non-coding RNA (lncRNA) in predicting variation in porcine intramuscular fat profile.

A method of using the long non-coding RNA (lncRNA) in predicting variation in porcine intramuscular fat profile in selecting and breeding pigs.

A method of using the long non-coding RNA (lncRNA) in predicting variation in porcine intramuscular fat profile in preparation of a kit adapted to detect variation of porcine intramuscular fat profile.

A method of using the kit in predicting variation in porcine intramuscular fat profile.

A method of using the kit in predicting variation in porcine intramuscular fat profile in selecting and breeding pigs.

A method of using the kit in predicting variation in porcine intramuscular fat profile in preparation of a kit adapted to detect variation of porcine intramuscular fat profile.

The disclosure further provides a kit adapted to detect variation in porcine intramuscular fat profile, the kit being adapted to detect expressions of a target gene of the lncRNA using a sequencing technique, a nucleic acid hybridization technique, a nucleic acid amplification technique, or an immunoassay technique. The target gene can be ROBO1.

The kit can comprise a pair of primers for amplification of the ROBO1 gene, and the sequences of the pair of primers are represented by SEQ ID NO: 4 and SEQ ID NO: 5.

The following uses are also provided:

A method of using the kit in predicting variation in porcine intramuscular fat profile.

A method of using the kit in predicting variation in porcine intramuscular fat profile in selecting and breeding pigs.

A method of using the kit in predicting variation in porcine intramuscular fat profile in preparation of a kit adapted to detect variation in porcine intramuscular fat profile.

The methods of the disclosure include but are not limited to any particular variants of XLOC_027632. In some embodiments, the variants contain at least 85% of the same or similar cDNA sequence of XLOC 027632, e.g., at least 90%, 91%, 92%, 93%, 94%, 95%, 96%, 97%, 98% or at least 99% of the sequences listed above are of the same or similar cDNA sequences.

The nucleic acid hybridization techniques as used in this disclosure include, but are not limited to, In-situ Hybridization (ISH), Microarrays, and Southern or Northern blots. The In-situ Hybridization (ISH) uses a labeled complementary DNA or RNA strand as a probe to locate a specific DNA or RNA sequence in a portion or section of the tissue, or the entire tissue (Tissue-wide ISH embedding) if the tissue is small enough. DNA ISH can determine the structure of a chromosome. RNA ISH is used to measure and locate mRNA and other transcripts (e.g., ncRNA) in tissue sections or in whole tissues. Sample cells and tissues are often preprocessed to immobilize the target transcript in situ and increase the entry of the probe. The probe hybridizes with the target sequence at elevated temperatures and then the excess probe is washed away. The base-labeled probes in tissues labeled with radioactive, fluorescence or antigen labels are located and quantified using autoradiography, fluorescence microscopy, or immunohistochemistry, respectively. ISH can also use two or more probes labeled with radioactive or other non-radioactive labels to simultaneously detect two or more transcripts.

In this disclosure, Laiwu pigs and Large white pigs are selected as experimental materials. The RNA-seq and bioinformatics methods are used to analyze the gene expression profiles of the intramuscular adipose tissue in Laiwu pigs and Large white pigs, and to identity and select the key differentially expressed lncRNA and its target genes related to adipogenic differentiation and lipid metabolism. The XLOC_027632 related to the content of the porcine intramuscular fat has been identified. The target gene ROBO1 in the differentially expressed lncRNA is predicted through co-expression network analysis and trans regulation. The molecular mechanism of regulating intramuscular fat deposition and the regulation of lipid metabolism of the gene are verified. The molecular markers in the disclosure can be used for breeding high meat quality livestock and poultry varieties.

DETAILED DESCRIPTION

To further illustrate, embodiments detailing a long non-coding RNA (lncRNA) and use thereof in selective breeding of pigs are described below. It should be noted that the following embodiments are intended to describe and not to limit the disclosure.

Example 1: Sample Collection, Preparation and Experimental Design

The experimental pigs, including Large white pig (D_JN) and Laiwu pig (L_JN), were slaughtered, and the intramuscular adipose tissues of the longissimus dorsi were collected, cut into small pieces, placed in a 5 mL cryotube, frozen in liquid nitrogen, and then stored in a 0° C. refrigerator for extraction of total RNA. The lncRNAs in the intramuscular adipose tissues of Large white pig (D_JN) and Laiwu pig (L_JN) were identified, and the gene expressions of the intramuscular adipose tissues were analyzed. The Large white pig (D_JN) and the Laiwu pig (L_JN) were both provided with three experimental groups, and each group was provided with three samples.

Example 2: Extraction and Quality Control of Total RNA of Samples

Equal amounts of cryopreserved adipose tissue samples were taken. The total RNA of each adipose tissue sample was extracted using a mirVana™ RNA extraction kit according to the instruction manual. The separated total RNAs were stored in a −80° C. refrigerator. The concentration of the RNAs and the OD 260 nm/OD 280 nm values were measured using a NanoDrop 2000 spectrophotometer and controlled at 1.9-2.1. The quality of total RNA was evaluated with Bioanalyzer 2100, and the RNA integrity number (RIN) was controlled >=7 and 28S/18S>=0.7. The potential genomic DNA contamination was removed using RNase-free DNase I.

Example 3: cDNA Library Construction and RNA Sequencing

The strand-specific cDNA library
(1) Removal of rRNA with Ribo-zero kit
(2) RNA fragmentation
(3) Double-stranded cDNA synthesis and purification
(4) End repair, adding nucleotide A
(5) Sequencing Connector Connection
(6) Enrichment and purification of DNA fragments
(7) Library Quality Inspection
(8) 6 cDNA libraries were established, namely D_JN_1, D_JN_2, D_JN_3 (cDNA library of intramuscular adipose tissue of Large white pig) and L_JN_1, L_JN_2, L_JN_3 (cDNA library of intramuscular adipose tissue of Laiwu pig).
RNA-Seq (Illumina Sequence)

The libraries were tested qualified. The Illumina Hi Seq™ 2500 sequencing platform was used to analyze the cDNA libraries by using the Paired-end Sequence, and the off-line data was the raw reads.

Example 4: Quality Control and Filtering of Raw Reads

Raw reads contain low quality and contaminated sequences that must be filtered out to ensure the accuracy and reliability of the subsequent bioinformatics analysis. The quality control of the raw reads was conducted using Cutadapt (v1.12) and FASTX_toolkit (v0.1.14) software. The subsequent analysis was all based on the clean reads.

The operations were as follows:
(1) removing the reads having an adapter sequence;
(2) filtering out the reads containing no more than 10% of the base (N);
(3) removing the low-quality reads in which the bases having a mass value Q<20 accounted for more than 15% of the total bases;

The results are shown in Table 1. Through the quality control, about 90 million clean reads were obtained in each sample, and contain around 95% of the bases having Q-score ≥30. The GC base content was about 50%. This indicated that the sequencing data results were reliable, and can be used for further analysis.

TABLE 1

| Samples | Raw reads | Clean reads | Valid ratio (base) | Q30 (%) | GC content (%) |
|---|---|---|---|---|---|
| Sample_D_JN_1 | 94261614 | 90180702 | 95.61% | 94.48% | 51.00% |
| Sample_D_JN_2 | 94457608 | 90392480 | 95.63% | 94.48% | 49.50% |
| Sample_D_JN_3 | 94739548 | 91093142 | 96.09% | 94.74% | 53.50% |
| Sample_L_JN_1 | 92489412 | 88890352 | 96.05% | 95.30% | 50.00% |
| Sample_L_JN_2 | 92272792 | 89083366 | 96.48% | 95.60% | 51.00% |
| Sample_L_JN_3 | 95371148 | 91659768 | 96.04% | 95.26% | 49.00% |

Example 5: Reference Genome Alignment and Transcript Splicing

The clean reads were aligned to the reference genome to locate the reads. Download the pig's reference genome Sscrofa 10.2 and the annotation file Sscrofa 10.2.87.chr.gtf from the Ensembl database. Then, use the bowtie software (v2.2.5) bowtie-build to establish the reference genome index, and use TopHat (v2.0.12) software to compare the clean reads obtained from each sample to the reference genome. The mismatch was set as 2, and others adopted default parameters.

To predict new transcripts, the transcripts required reconstruction and assembly. Inputting the sequence alignment file accepted_hit. bam obtained after aligning the clean reads to the genome using the TopHat2 software. Using Cufflinks (v2.1.1) software to assemble transcripts for each sample to get the annotation file named transcript.gtf. Using Cuffmerge to assemble the gtf. files of 12 samples and merge them to generate the annotation file of merged_transcript.gtf. Using Cuffcompare to compare merged transcript.gtf with the reference annotation file Sscrofa10.2.87. chr.gtf one by one, selecting the transcripts that matched or were similar to known ncRNAs, mRNAs, etc., locating the location information of the transcripts, and predicting the potential new mRNA and lncRNA.

Results: Clean reads were compared to the pig's reference genome using bioinformatics software. The results are shown in Table 2.

TABLE 2

| | | | Mapped types | |
|---|---|---|---|---|
| Samples | Total reads | Total Mapped reads | Multiple mapped reads | Uniquely mapped reads |
| Sample_D_JN_1 | 90180702 | 68721069 (76.2%) | 11568665 (12.83%) | 57152404 (63.38%) |
| Sample_D_JN_2 | 90392480 | 90392480 (76.31%) | 11136845 (12.32%) | 57838075 (63.99%) |
| Sample_D_JN_3 | 91093142 | 69180297 (75.94%) | 14614985 (16.04%) | 54565312 (59.9%)) |
| Sample_L_JN_1 | 88890352 | 65333853 (73.5%) | 11406632 (12.83%) | 53927221 (60.67%) |
| Sample_L_JN_2 | 89083366 | 65710645 (73.76%) | 10421104 (11.7%) | 55289541 (62.06%) |
| Sample_L_JN_3 | 91659768 | 67630486 (73.78%) | 11270084 (12.3%) | 56360402 (61.49%) |

Example 6: Analysis of Alternative Splicing Events

Using ASprofile (v1.0) software to analyze the assembly files of each sample, and statistically classifying the variable splicing events. According to the structure of the exons and the status of the intron retention, the alternative splicing (AS) events were defined into 12 different categories, including TSS, TTS, SKIP, XSKIP, MSKIP, XMSKIP, IR, XIR, MIR, XMIR, AE, XAE.

Example 7: Selection and Identification of Potential lncRNA

LncRNA is a class of RNA that is longer than 200 bp and does not encode proteins. The potential lncRNA can be identified based on the two main characteristics, and comprises intergenic lncRNA (lincRNA), intronic lncRNA, sense lncRNA and antisense lncRNA. The operations are as follows:

(1) Exon number and transcript length selection: the threshold was exon number ≥2, length >200 bp, and the single exon transcript of low-confidence was filtered out.

(2) Coding potential selection: for the above selected transcripts, using software PLEK (Li et al., 2014), CNCI (Sun et al., 2013b), CPC (Kong et al., 2007), Pfam (Finn et al., 2014) to predict their protein-coding potential, and analyzing the intersection to obtain the lncRNA. PLEK was based on optimized k-mer strategy, threshold score <0. CNCI was based on triplet spectrum of sequence adjacent nucleotides, threshold score <0. CPC was based on the sequence characteristics of the open reading frame of transcripts, and the sequence characteristics were also compared with UniProt reference database BLASTX, threshold score <0. Pfam was a protein family database, and can homologously match the transcript coding frame with the database; the transcript that was not matched was lncRNA.

(3) The identification of lncRNA: ALB (A Domestic-Animal Long Noncoding RNA Database) was a database of livestock animal lncRNA, and the candidate lncRNA was compared with the lncRNA in the database by BLASTN tool. The selected lncRNAs were identified strictly under the conditions of Identity=100%, mismatch=0, E-value <1e-10, and gap_opening=0.

The classification, length distribution and number of exons of the lncRNAs were analyzed and compared with the identified mRNAs. The length distribution trend of the lncRNAs and the protein-encoding genes was roughly consistent, and the transcription density of the shorter mRNA was higher than that of the lncRNAs. The average length of the lncRNAs identified in this study was 2263 nt, and the average length of the mRNA was 2028 nt.

Example 8: Analysis of Gene Differential Expression Between Different Samples Building data sets of known mRNA, predicted new transcripts, and lncRNA. Using bowtie and eXpress software to compare and statistically analyze the read count of each transcript in each sample. The gene expression level was corrected using the fragment per kb per Million reads (FPKM) algorithm to eliminate the effects of sequencing depth, gene length and sample differences on the gene expression. The experiment was biologically repetitive. Using the R language package DESeq2 (Anders & Huber, 2010) to analyze the differential expression of genes (including lncRNA, mRNA) between different samples based on the negative binomial distribution. Benjamini-Hochberg algorithm was used for multiple hypothesis test calibration of P values to obtain a corrected P value (padj). The differentially expressed genes were selected under the condition of |log 2FoldChange|≥1 (L_JN vs D_JN) and padj≤0.05.

Based on the expression value FPKM of the transcripts, constructing a FPKM boxplot and density map to analyze the integral expression of the transcripts in the samples of different adipose tissues. The distribution of the expression of the transcripts in the intramuscular adipose tissue of the two breeds of pigs in the group were consistent. Compared with Laiwu pig, there were lower expression transcripts in the adipose tissue of Large white pig between groups. Analysis of the expression level of transcripts between samples shows that the experimental data basically meets the requirements. At the same time, the analysis of the expression levels of the identified lncRNA and mRNA shows that mRNA has a relatively high expression level, and the expression level of lncRNA is low. The FPKM values are mainly between (0 and 10), and the mRNA with FPKM value of 0-100 are evenly distributed.

Figure 1:
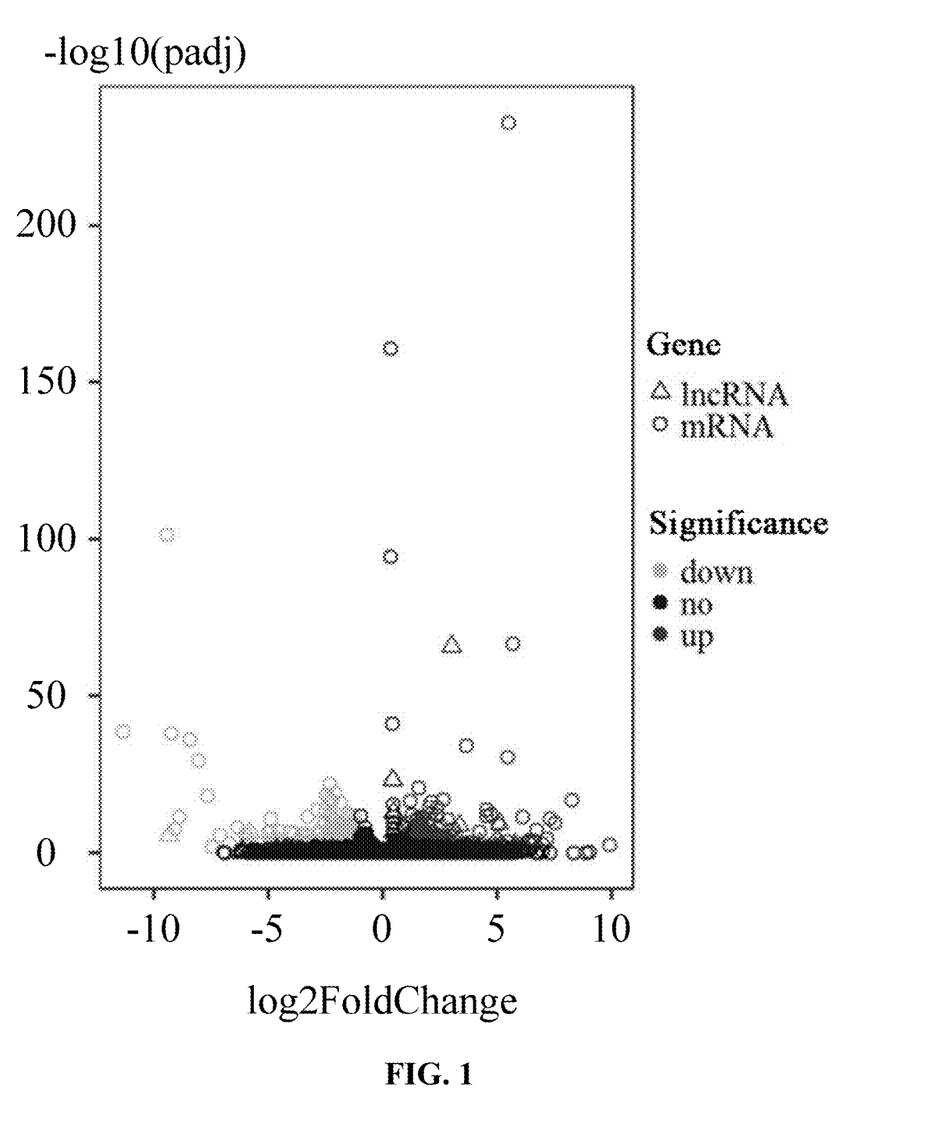
FIG. 1 is a distribution map of differentially expressed genes in intramuscular fat.

By differentially analyzing the intramuscular adipose tissue (L_JN vs D_JN) gene (FIG. 1), 56 differentially expressed lncRNAs (34 up-regulated, 22 down-regulated) and 715 differentially expressed mRNAs (371 up-regulated, 344 down-regulated) were identified, of which genes with more than 4 times of difference accounted for about 48.4%. Among them, differentially expressed genes represented by BRCA1 and JAML and differentially expressed long noncoding RNA represented by XLOC_027632 were selected for further analysis.

Example 9: Differential Expression Gene GO and KEGG Pathway Enrichment Analysis Gene Ontology (GO) is an international classification standard for gene function, which is composed of molecular function, biological process, and cellular component. The Pathway Enrichment Analysis can identify the major metabolic pathways and signaling pathways of differentially expressed genes. As the main public database of correlation, the KEGG (Kyoto Encyclopedia of Genes and Genomes) database is a main tool for metabolic analysis and regulation network research. To study the main biological functions of differentially expressed genes, the experiment used CluGO software to calculate the GO terms and signal pathways with significantly enriched differentially expressed genes based on hypergeometric distribution test. The P value (Q_value) was corrected by the Benjamini-Hochberg algorithm. The enrichment was significant when Q_value ≤0.05.

513 database-annotated differentially expressed genes were identified in the intramuscular adipose tissue of Large white pig and Laiwu pig, and 210, 144, and 62 genes were enriched into one or multiple terms of the biological processes, molecular functions, and cellular components, respectively. A large number of GO terms closely related to lipid metabolism and deposition were significantly enriched. According to the bioprocess, more genes (≥15) were enriched in the lipid biosynthetic process, the lipid metabolic process, the cellular lipid metabolic process, response to lipid, MAPK cascade, positive regulation of MAPK cascade, and regulation of MAPK cascade. For the molecular functional part, it was only significantly enriched in the enzyme inhibitor activity. In the cellular components, it was significantly enriched in related GO terms such as extracellular matrix, axon. There were significant differences in intramuscular fat deposition between Large white pig and Laiwu pig. It was found by GO annotation that differentially expressed genes were significantly enriched in biological processes of lipid metabolism and cell differentiation, indicating the intramuscular fat deposition and metabolism were regulated by different genes.

Example 10: Differentially Expressed Gene Protein—Protein Interaction Network (PPI Network) Analysis The PPI network studies can reveal the function of proteins at the molecular level. Therefore, based on the interaction relationship in the STRING protein interaction database, the PPI network analysis of differentially expressed genes was carried out to further explore the complex interaction between the proteins encoded by differentially expressed genes in the muscle adipose tissue of Large white pig and Laiwu pig. The STRING database contains the breeding pig (Sus scrofa), and the interaction relationship of the differential gene set list can be extracted directly from the database. The Cytoscape software was used to visually analyze the data files of the obtained differential gene coded protein interaction network. In the protein interaction network diagram, the node represents the protein, the edge represents the interaction relationship between proteins, and the degree represents the number of proteins interacting with a specific node. The node size is proportional to the degree of the node. The color of the node indicates the log 2FoldChange value of the differentially expressed gene.

Example 11: Prediction of Target Gene of Differentially Expressed lncRNA

As a non-coding RNA, lncRNA mainly functions in the regulation of target genes, including trans-regulation on the distant protein-coding genes. The genes with the same expression pattern have a strong functional correlation. Therefore, the target genes of the lncRNA can be identified by studying the co-expression and trans-regulation of the lncRNA and the mRNA.

The co-expression relationship between the lncRNA and the mRNA was analyzed by calculating the Pearson correlation coefficient (PCC) of the differential expression amount of the lncRNA and the mRNA. The co-expressed lncRNA-mRNA was selected with |PCC|>0.8 and P_value <0.05 as the threshold.

lncRNA trans target gene analysis: predict the trans target gene of differentially expressed lncRNA through the interaction relationship between the lncRNA and the mRNA. RNAplex software was used to calculate the binding free energy (Energy) between the lncRNA and the mRNA, and in combination with co-expression results, to identify the lncRNA trans target gene when Energy <−20 and |PCC|≥0.9.

The fat metabolism-related trans-target genes BRCA1 and JAML of the XLOC_027632 were found. The expression of the genes BRCA1 and JAML in the intramuscular fat of Laiwu pig was higher than that of Large white pig.

Example 12: Fluorescence Quantitative PCR Verification of Differentially Expressed lncRNA 9 differentially expressed genes (4 lncRNAs and 5 mRNAs) were randomly selected from L_JN (Intramuscular tissue of Laiwu pigs) vs D_JN (intramuscular tissue of Large white pigs). Each gene was provided with 3 biological repetitions. The expression level of the genes was measured by qRT-PCR method with the actin beta (ACTB) gene as the internal reference. The cDNA template was synthesized from about 0.5 μg of RNA sample through reverse transcription by PCR System 9700 (Applied Biosystems, USA). The qRT-PCR analysis was performed using Green PCR Kit (Qiagen, Germany) 480II Real-time PCR Instrument (Roche, Swiss).

The RNA to be tested was reversely transcribed into cDNA using HiScript II Q RT SuperMix for qPCR (+gDNA wiper) (Vazyme, R223-01).

(1) The total RNA sample stored in a −80° C. refrigerator was taken out, thawed at room temperature. The reverse transcription system in a 0.2 mL PCR tube was prepared as follows.

(2) Reverse Transcription System (10 μL): total RNA, 0.5 μg; 4×gDNA wiper Mix, 2 μL; adding Nuclease-free $H_2O$ to 8 μL, Reaction conditions: 42° C. for 2 min. Adding 5× HiScript II Q RT SuperMix IIa, 2 μL, Reaction conditions: 25° C. for 10 min, 50° C. for 30 min, 85° C. for 5 min.

(3) Following the reverse transcription, the reverse transcription system was diluted with Nuclease-free $H_2O$ to a total volume of 100 μL and stored at −20° C.

Real-Time PCR Reaction (1) Compositions and Volumes

TABLE 3

| Components and volume in PCR | |
|---|---|
| Components | Volume (μL) |
| 2xQuantiFast SYBR Green PCR Master Mix | 5 |
| Forward primer (10 μM) | 0.2 |
| Reverse primer (10 μM) | 0.2 |
| Nuclease-free $H_2O$ | 3.6 |
| cDNA | 1 |
| Total | 10 |

(2) Cycling Conditions

TABLE 4

| Cycling conditions of PCR | | | |
|---|---|---|---|
| Steps | Temperature (° C.) | Time | Cycle number |
| Initial denaturation | 95 | 10 min | 1 |
| Denaturation | 95 | 10 s | 40 |
| Annealing | 60 | 30 s | |
| Dissociation | 60 to 97 | | 1 |

(3) The compositions were uniformly mixed, centrifuged, distributed on a 384-well plate, and transferred to LightCycler® 480 II Real-time PCR Instrument (Roche, Swiss) for qRT-PCR reaction and analysis.

The relative expression of genes in each group of samples was calculated by 2-ΔΔ Ct method. The relative expression amount was statistically analyzed by t-test. The data were expressed as mean±standard deviation (Mean±SD), where P<0.05 indicated that the difference was significant.

Figure 2:
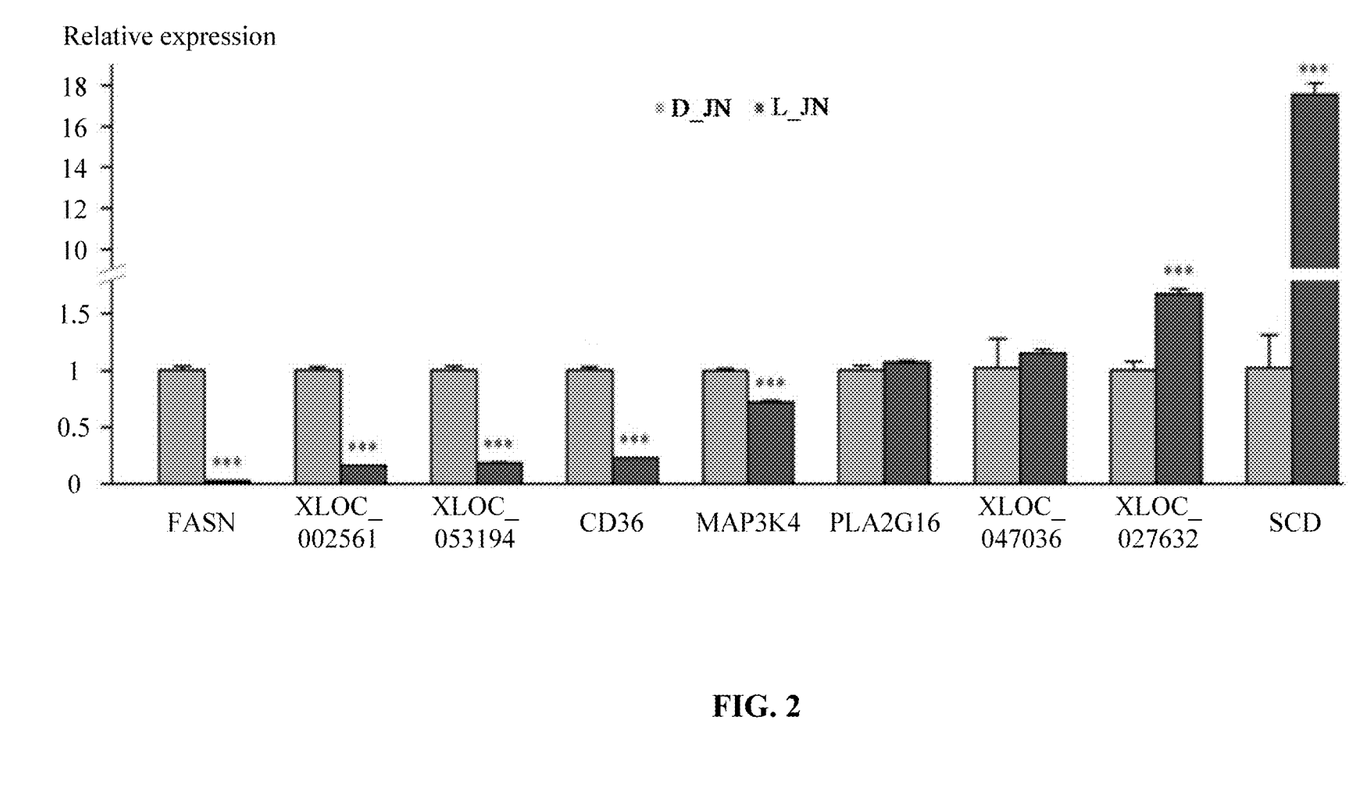
FIG. 2 is a diagram showing the results of qRT-PCR verification of differentially expressed genes.

FASN, XLOC_002561, XLOC_053194, CD36, and MAP3K4 were significantly up-regulated in the intramuscular fat of Large white pigs. The expression of XLOC_027632 and SCD were significantly up-regulated in the intramuscular fat of Laiwu pig (FIG. 2). The above results were consistent with the sequencing results, indicating that the sequencing results were reliable. 10 intramuscular tissue samples of Large white pigs and 10 intramuscular tissue samples of Laiwu pig were randomly selected for the fluorescence quantitative verification of the candidate genes XLOC_027632 and ROBO1. The operations were the same as above.

Primer Design:

```
XLOC_027632:
Upstream primer:
5'-aaatgggaagtgaatcctgag-3'    (SEQ ID NO. 2)
```

-continued

```
Downstream primer:
5'-ttccaagttgcttgtaggct-3'      (SEQ ID NO. 3)

ROBO1 gene:
Upstream primer:
5'-tcctcctcatagtaatagt-3'       (SEQ ID NO. 4)

Downstream primer:
5'-ttcatcttcctcttcttc-3'        (SEQ ID NO. 5)
```

Figure 3:
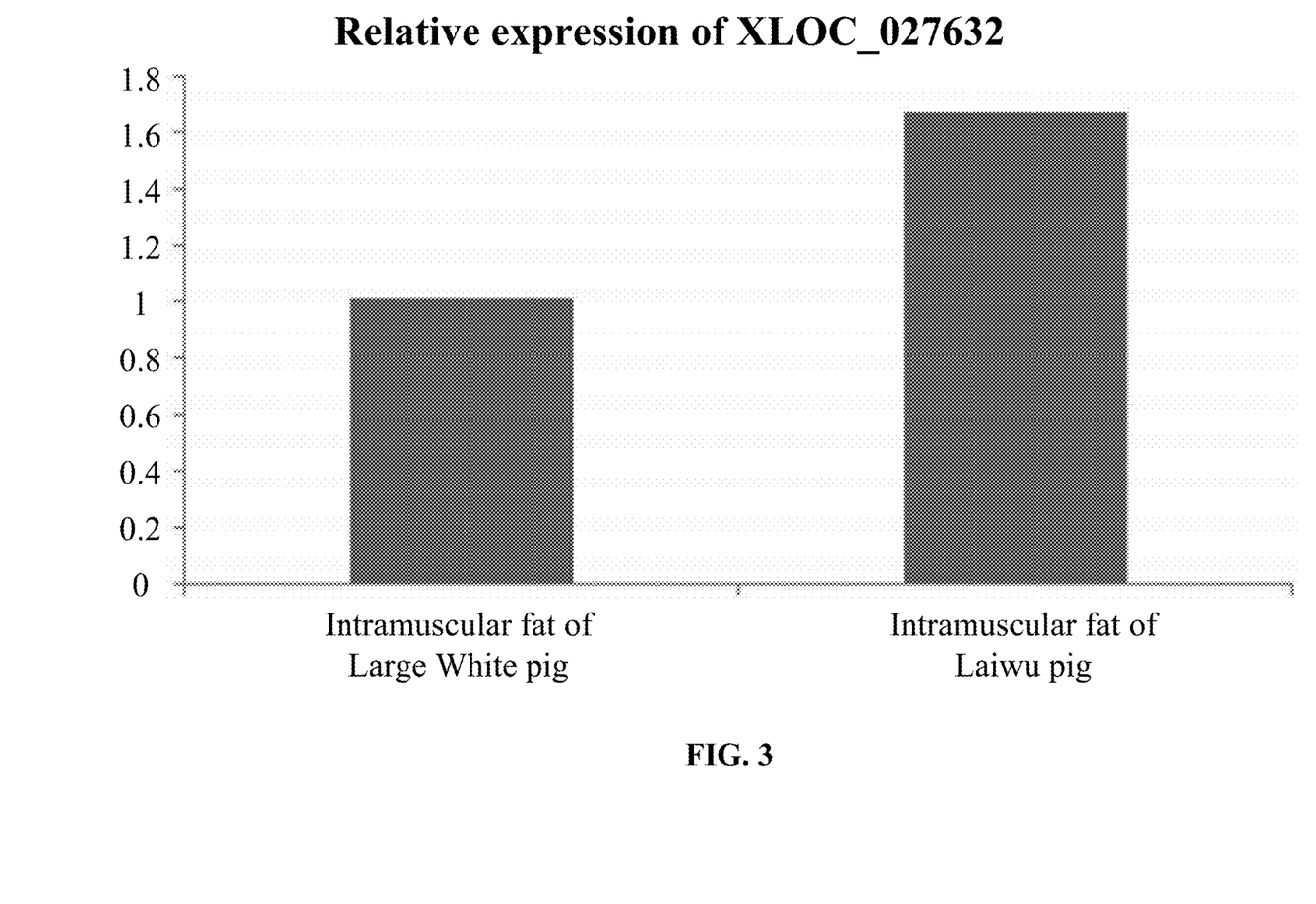
FIG. 3 is a diagram showing the results of qRT-PCR verification of the differentially expressed gene XLOC_027632.

The results are shown in FIG. 3. The expression of XLOC_027632 in the intramuscular fat of Laiwu pig is about 2 times that of the intramuscular adipose tissue of Large white pig. The ROBO1 gene in the intramuscular fat of Laiwu pig is about twice as much as that in the intramuscular adipose tissue of Large white pig.

It will be obvious to those skilled in the art that changes and modifications may be made, and therefore, the aim in the appended claims is to cover all such changes and modifications.

What is claimed is:

1. A kit adapted to detect variation of porcine intramuscular fat profile, the kit being adapted to detect expressions of a long non-coding RNA (lncRNA) XLOC_027632 having more than 90% sequence homology with SEQ ID NO: 1, the kit comprising a pair of primers for nucleic acid amplification, wherein the sequences of said primers are represented by SEQ ID NO: 2 and SEQ ID NO: 3.

2. The kit of claim 1, wherein the kit is adapted to detect a tissue comprising intramuscular adipose tissue.

* * * * *

SEQUENCE LISTING

<160> NUMBER OF SEQ ID NOS: 5

<210> SEQ ID NO 1
<211> LENGTH: 1946
<212> TYPE: DNA
<213> ORGANISM: Artificial Sequence
<220> FEATURE:
<223> OTHER INFORMATION: Fully synthetic

<400> SEQUENCE: 1

```
ccgccgctcc catcctgaca gtgaggaagt ccatttcggg tgttcctgca ggtaggggtg      60
gaggagtctg tcagcgcctg caattctcct tctgaagctg aaggggctt ttagtttcaa      120 ttacttctgt gctgggtcga ggaaggaatg gaaccacacc cctcagccac gaatacctcc     180
tccagtgccc gaaggaaaac ggcgtaattg aaaacgttgt cagcggcaca cgtccatttt     240
taacttgagt ggcttctttt ctgggtggaa gagagcggta tcagaccagg ggtgagcagt     300
tgaaggagga atgaacaaaa ggcttgcgcc acggctgctc tggctttgtg cggttttttt     360
gttggttttt tttttttttt tttcagttgc atttgtgcat tgttacaaca cggtttagac     420
tgtaggccct ccggagggca ggcttgtgcc cacgagaaag gtaaacctcc cgggaatata     480
atctacgtaa tacactgtac acaaataagc cgcggacggt tttggatgat gacaggagat     540
ttccctctgg agtagtttaa gattctaatg ttccacttac aggattagac caaggattaa     600
ggaccaagaa atataattaa aaaaaaaaaa aagattaaaa cctggaaagc ctagaacaac     660
ttctcaaagt gtgcttcaca attacttgga acacttgtta aagcacagca tgctgggctg     720
catcccctga agttctctga ttaggttgtc tggagcctgg taatttgcat ttctaccaag     780
ttcccaagtg atggtctgga cctcccccac ccaccaaact agaaagttaa tagctttctt     840
cttcattagg cttatctttt gataaagcgt gtagatttac ttatctgcaa ctgaaacaga     900 aatcctttc ctaaggatgt cttattattc cagaagatca catagcaatg gttagaccaa     960 actggggat gaaatacagg tttttcattc gtttggtaca taagaattgc tcacccactc     1020
tcttatgaca gagatatgct caccctgaat atccagtagg cacaaaaaa ggtaaggtct     1080 ctgttgtaga gtttacagtt aagtgagaaa acatacaaat tgcattaaga gcagtagaaa     1140
tcacaaaatt gggctacaag aaatgaggag tgggagaatg gaaaggaggt aaaaggcagg     1200
gcactgaaaa gctaagggct gtaggatggt aggcgatctg ggaagggtg agaaagaagg     1260 aaacctccag gaagtgggaa tagcaagagt caaggccctg agaccagaag gagcttggct     1320
tcttctacaa gttgaagaaa gatgcaagtg gccaaagtga aatgagccat ggcagatgaa     1380
atgggaagtg aatcctgaga gataaggaag aatcaaacaa tgcaaagatt cgtagatttc     1440
tctaagcgtc ttaaaagttt agcctacaag caacttggaa gccatcagag acttaagcaa     1500
tgaaatgttg tggcagcttt ttgttttgtt ctattttttcc ctacatgtag aagatgctgt     1560
atgaggattc tttgctgcct tttccgccat caggtattta agatcatttg ggagagcagg     1620
```

```
tgcttgaaga ttagctccga cagaagaggg agatgtggat tggttggagt agagtaaagg    1680
gtttcctgca tcacagtgga tttgctgaga tcccactctt tttgaaggaa actactctgg    1740
accaatggaa atggttaaac cataggatta tattacttt cgtttgtggg cacatccagg     1800
tggaaataag tacttgcatt cttatcagca gaaggaaaat ttttagcata taggaagaac    1860
tattgtcagc atctgtggaa aaagccttag ctttactccc ccatggaaga aagcaaacga    1920
aagccgcccc atgaatttaa catgat                                          1946

<210> SEQ ID NO 2
<211> LENGTH: 21
<212> TYPE: DNA
<213> ORGANISM: Artificial Sequence
<220> FEATURE:
<223> OTHER INFORMATION: Fully synthetic

<400> SEQUENCE: 2
aaatgggaag tgaatcctga g                                                21

<210> SEQ ID NO 3
<211> LENGTH: 20
<212> TYPE: DNA
<213> ORGANISM: Artificial Sequence
<220> FEATURE:
<223> OTHER INFORMATION: Fully synthetic

<400> SEQUENCE: 3
ttccaagttg cttgtaggct                                                  20

<210> SEQ ID NO 4
<211> LENGTH: 19
<212> TYPE: DNA
<213> ORGANISM: Artificial Sequence
<220> FEATURE:
<223> OTHER INFORMATION: Fully synthetic

<400> SEQUENCE: 4
tcctcctcat agtaatagt                                                   19

<210> SEQ ID NO 5
<211> LENGTH: 18
<212> TYPE: DNA
<213> ORGANISM: Artificial Sequence
<220> FEATURE:
<223> OTHER INFORMATION: Fully synthetic

<400> SEQUENCE: 5
ttcatcttcc tcttcttc                                                    18
```